United States Patent
Krause et al.

(10) Patent No.: US 9,156,005 B2
(45) Date of Patent: *Oct. 13, 2015

(54) HOLLOW FIBER MEMBRANE AND METHOD FOR MANUFACTURING THEREOF

(71) Applicant: Gambro Lundia AB, Lund (SE)

(72) Inventors: Bernd Krause, Rangendingen (DE); Hermann Gohl, Bisingen (DE); Markus Hornung, Nehren (DE); Carina Zweigart, Schomberg (DE)

(73) Assignee: Gambro Lundia AB, Lund (SE)

( * ) Notice: Subject to any disclaimer, the term of this patent is extended or adjusted under 35 U.S.C. 154(b) by 109 days.

This patent is subject to a terminal disclaimer.

(21) Appl. No.: 14/017,349

(22) Filed: Sep. 4, 2013

(65) Prior Publication Data

US 2014/0001115 A1    Jan. 2, 2014
US 2015/0273400 A9    Oct. 1, 2015

Related U.S. Application Data

(62) Division of application No. 12/446,058, filed as application No. PCT/EP2007/060838 on Oct. 11, 2007, now Pat. No. 8,596,467.

(60) Provisional application No. 60/829,965, filed on Oct. 18, 2006.

(30) Foreign Application Priority Data

Oct. 18, 2006 (SE) ...................................... 0602189

(51) Int. Cl.
*B01D 63/02* (2006.01)
*B01D 69/08* (2006.01)
(Continued)

(52) U.S. Cl.
CPC ............... *B01D 69/08* (2013.01); *B01D 63/02* (2013.01); *B01D 69/02* (2013.01); *B01D 69/087* (2013.01);
(Continued)

(58) Field of Classification Search
CPC ......... A61M 1/16; B01D 63/02; B01D 69/02; B01D 69/08; B01D 69/087; B01D 71/44; B01D 71/68; B01D 2323/08; B01D 2323/12; B01D 2323/22; B01D 2325/022; A61B 5/14525
See application file for complete search history.

(56) References Cited

U.S. PATENT DOCUMENTS 4,220,543 A   9/1980   Yamashita
4,269,713 A   5/1981   Yamashita et al.
(Continued)

FOREIGN PATENT DOCUMENTS

DE   198 17 364 C1   7/1999
DE   199 13 416 A1   10/2000
(Continued)

OTHER PUBLICATIONS

"The Filtration Spectrum" (Chart), Good Water Company, After Osmonics Inc, 1984, PP1.*

*Primary Examiner* — David C Mellon
(74) *Attorney, Agent, or Firm* — K&L Gates LLP

(57) ABSTRACT

The present invention concerns a semipermeable hollow fiber membrane having an outer wall surface, an inner wall surface and an interior lumen extending along the length thereof and having the selective layer on the outer wall surface with a surface roughness below 10 nm. According to the invention the membrane has the smallest pore size on the outer wall surface, and has an outer wall surface which is smooth, continuous and homogeneous in a nanoscopic scale and four to five distinct layers of different pore size and density. Further the present invention concerns a process for manufacturing thereof and the use thereof.

10 Claims, 7 Drawing Sheets

(51) Int. Cl.
*A61M 1/16* (2006.01)
*B01D 71/44* (2006.01)
*B01D 71/68* (2006.01)
*B01D 69/02* (2006.01)
*A61B 5/145* (2006.01)

(52) U.S. Cl.
CPC ........... *B01D 71/44* (2013.01); *B01D 71/68* (2013.01); *A61B 5/14525* (2013.01); *A61M 1/16* (2013.01); *B01D 2323/06* (2013.01); *B01D 2323/08* (2013.01); *B01D 2323/12* (2013.01); *B01D 2323/22* (2013.01); *B01D 2325/022* (2013.01)

(56) References Cited

U.S. PATENT DOCUMENTS

| | | | |
|---|---|---|---|
| 4,286,015 A | 8/1981 | Yoshida et al. | |
| 4,317,729 A | 3/1982 | Yamashita et al. | |
| 4,387,024 A | 6/1983 | Kurihara et al. | |
| 4,713,292 A | 12/1987 | Takemura et al. | |
| 4,822,489 A | 4/1989 | Nohmi et al. | |
| 4,935,141 A | 6/1990 | Buck et al. | |
| 5,702,503 A | 12/1997 | Tang | |
| 5,706,806 A * | 1/1998 | Kissinger | 600/309 |
| 5,762,798 A | 6/1998 | Wenthold et al. | |
| 6,284,137 B1 | 9/2001 | Hajikano et al. | |
| 6,355,730 B1 | 3/2002 | Kozawa et al. | |
| 6,802,820 B1 | 10/2004 | Gorsuch et al. | |
| 2003/0141242 A1 | 7/2003 | Kurth et al. | |
| 2005/0242021 A1 | 11/2005 | Ditter et al. | |

FOREIGN PATENT DOCUMENTS

| | | |
|---|---|---|
| EP | 0 082 433 B2 | 6/1983 |
| EP | 0 305 787 B1 | 10/1992 |
| EP | 0 168 783 B1 | 6/1994 |
| EP | 0 568 045 B1 | 10/1996 |
| EP | 0 824 960 A1 | 2/1998 |
| EP | 1 535 636 A1 | 5/2005 |
| EP | 1 535 636 A1 | 6/2005 |
| EP | 1 547 628 A1 | 6/2005 |
| EP | 1 634 610 A1 | 3/2006 |
| WO | WO 86/00028 | 1/1986 |
| WO | WO 90/04609 | 5/1990 |
| WO | WO 94/00222 | 1/1994 |
| WO | WO 94/29002 | 12/1994 |
| WO | WO 01/78805 A1 | 10/2001 |
| WO | WO 03/097221 A2 | 11/2003 |
| WO | WO 2004/056460 | 7/2004 |
| WO | WO 2004/056460 A1 | 7/2004 |

* cited by examiner

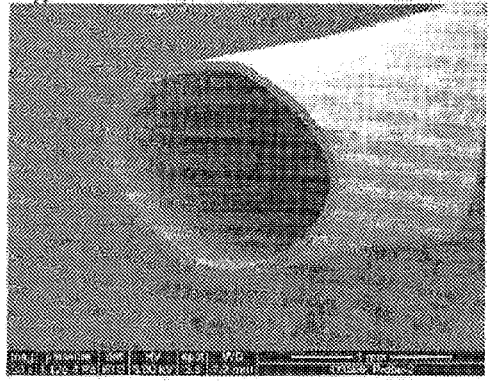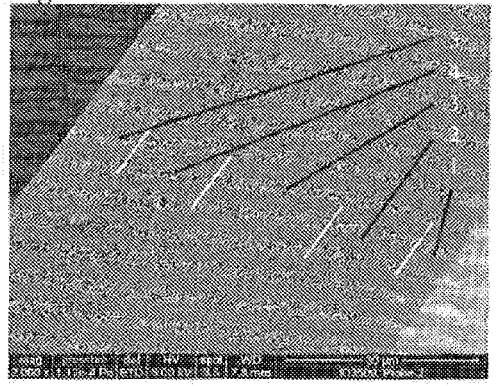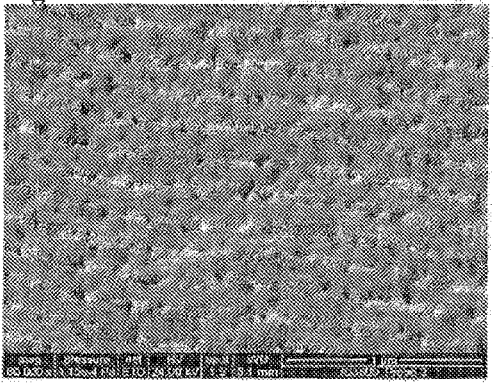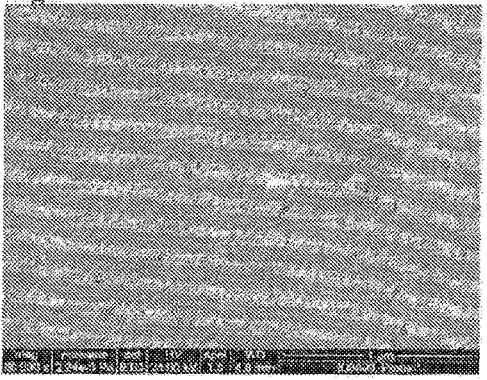

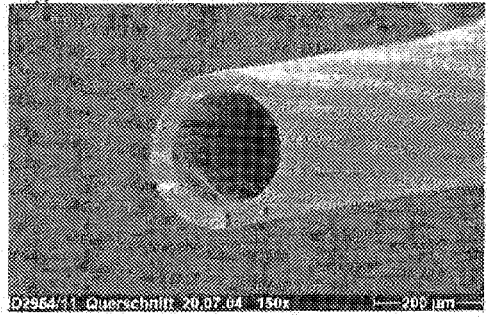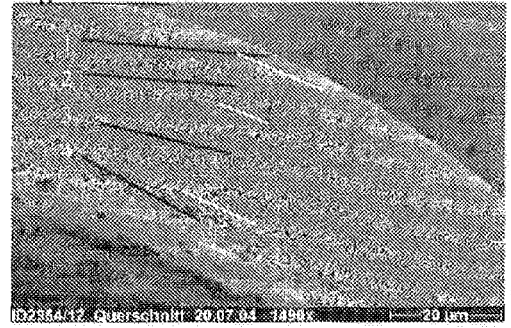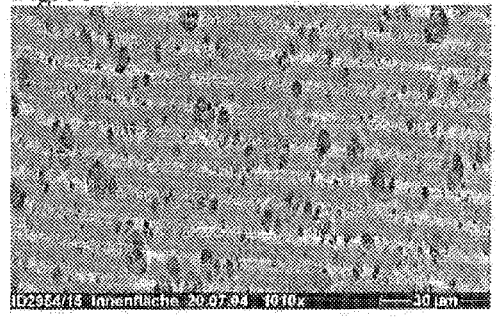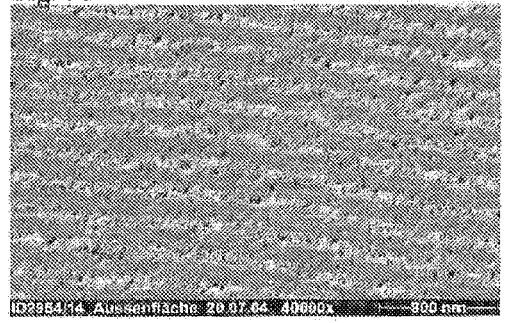

Inside

Outside

HOLLOW FIBER MEMBRANE AND METHOD FOR MANUFACTURING THEREOF

CROSS REFERENCE TO RELATED APPLICATIONS

This application is a divisional of U.S. patent application Ser. No. 12/446,058, filed Oct. 18, 2010, which claims the benefit of priority to International Application No. PCT/EP2007/060838, filed Oct. 11, 2007, which claims the priority of Swedish Patent Application No. 0602189-3, filed Oct. 18, 2006; and claims the benefit of U.S. Provisional Application No. 60/829,965, filed Oct. 18, 2006, the contents of all of which are incorporated herein by reference.

TECHNICAL FIELD

The present invention concerns a semi-permeable hollow fiber membrane having an outer wall surface, an inner wall surface and an interior lumen extending along the length thereof. More particular it relates to a membrane having the selective layer on the outer wall surface.

BACKGROUND OF THE INVENTION

Semi-permeable hollow fiber membranes are known in detail in, for example, EP-A-0 568 045, EP-A-0 168 783, EP-B-0 082 433, WO 86/00028, and EP 0 824 960. These membranes are manufactured from polymeric synthetic materials, they have asymmetric structure with high diffusive permeability (clearance) and have water filtration capability with ultrafiltration in the range of low flux to high flux. In EP-A-0 305 787, a 3-layer structure membrane and filter with corresponding performance, is disclosed.

The membranes according to prior art are well performing, but still have some space for improvement and optimization.

One limiting feature of these membranes are that the fluid to be filtered is intended to flow in the interior lumen of the hollow fiber and the filtrate to go through the fiber wall from the lumen side to the outer wall side. In order not to have these filters to foul or clog, the dimensions of the hollow fiber, such as inner diameter, wall thickness and so on, have to be big enough to allow a good and high flow within the hollow fiber lumen.

In DE 199 13 416 it is suggested to make the filtration from outside to inside, i.e., to have the selective layer on the outside.

However, when working with body fluids like blood it is of most importance that the membrane surface, which is intended to be brought in contact with the body fluid, is as smooth as possible, has low protein adsorption, high biocompatibility, and a low thrombogenicity.

DESCRIPTION OF THE INVENTION

The present invention concerns a semipermeable hollow fiber membrane having an outer wall surface, an inner wall surface and an interior lumen extending along the length thereof and having the selective layer on the outer wall surface. According to the invention, the membrane has the smallest pore size on the outer wall surface, and has an outer wall surface which is smooth, continuous and homogeneous in a nanoscopic scale, being virtually devoid of roughness with a roughness parameter $R_a$ and $R_q$ of not more than 10 nm, the roughness being measured with the use of atomic force microscope (AFM), and calculating the roughness parameters $R_a$ and $R_q$ using the following equations:

$$R_a = \frac{1}{N}\sum_{i=1}^{N}|Z_i|$$

$$R_q = \sqrt{\frac{1}{N}\sum_{i=1}^{N}Z_i^2}$$

with N being the total number of data points and $Z_i$ being the height of a data point above the average picture level. With this smooth outer surface, the combination of the polymer system used and the membrane formation conditions, low thrombogenicity of the membrane is achieved. The extremely smooth surface does inhibit haemolysis if used in direct blood contact. Blood cells will not be ruptured during the contact with the smooth surface. The smoothness further reduces the interaction with proteins and the adsorption of proteins on the outer surface of the hollow fiber membrane.

In one embodiment the hollow fiber membrane wall has at least four layers with different pore sizes and mass densities, and wherein the layer positioned closest to the middle of the membrane wall has smaller pore size and higher mass density than the two layers directly adjacent on both sides, inner and outer, of this layer. With this structure, physical stability of the membrane is maintained even though the membrane has a small inner diameter and a small wall thickness. It further allows for tailoring the separation characteristics, i.e. cut-off and hydraulic permeability, by changing the structural density and pore size of the outer layer and the middle layer.

In another embodiment the hollow fiber membrane wall has four layers with different pore sizes and mass densities. A first layer, at the outer wall surface, has the smallest pore size and the highest mass density. A second layer, adjacent the first layer and placed on the inside facing side of the first layer, has larger pore size and lower mass density than the first layer. A third layer, adjacent the second layer and placed on the inside facing side of the second layer, has smaller pore size and higher mass density than the second layer, but larger pore size and lower mass density than the first layer. A fourth layer, at the inner wall surface and adjacent the third layer and placed on the inside facing side of the third layer, has larger pore size and lower mass density than the first, second and third layer. With this structure the degree of openness on the inner lumen side of the hollow fiber can be increased, which gives the possibility to increase diffusive transport properties if required. Also vortex like fluid flow can be achieved directly on the inner lumen side, which is advantageous for the mass transport phenomenon.

In an additional embodiment the hollow fiber membrane wall has five layers with different pore sizes and mass densities. A first layer, at the outer wall surface, has the smallest pore size and the highest mass density. A second layer, adjacent the first layer and placed on the inside facing side of the first layer, has larger pore size and lower mass density than the first layer. A third layer, adjacent the second layer and placed on the inside facing side of the second layer, has smaller pore size and higher mass density than the second layer, but larger pore size and lower mass density than the first layer. A fourth layer, adjacent the third layer and placed on the inside facing side of the third layer, has larger pore size and lower mass density than the first, second and third layer. A fifth layer, at the inner wall surface and adjacent the fourth layer and placed on the inside facing side of the fourth layer, has larger pore size and lower mass density than the first, second, third, and fourth layer. With this structure the degree of openness on the inner lumen side of the hollow fiber can be increased, which gives the possibility to increase diffusive transport properties if required. Also vortex like fluid flow can be achieved directly on the inner lumen side, which is advantageous for the mass transport phenomenon.

In another embodiment the hollow fiber membrane wall has five layers with different pore sizes and mass densities. A first layer, at the outer wall surface, has the smallest pore size and the highest mass density. A second layer, adjacent the first layer and placed on the inside facing side of the first layer, has larger pore size and lower mass density than the first layer. A third layer, adjacent the second layer and placed on the inside facing side of the second layer, has smaller pore size and higher mass density than the second layer, but larger pore size and lower mass density than the first layer. A fourth layer, adjacent the third layer and placed on the inside facing side of the third layer, has larger pore size and lower mass density than the first, second and third layers. A fifth layer, at the inner wall surface and adjacent the fourth layer and placed on the inside facing side of the fourth layer, has smaller pore size and higher mass density than the fourth layer. With this structure the inner surface can also be equipped with a smooth inner surface, which is required if two fluid systems, having high fouling potential, are passed on the inside and the outside, respectively, of the hollow fiber membrane. The smooth inner surface reduces the risk of haemolysis (in the case of blood contact) and the risk of fouling and the adsorption of substances on the surface. In addition to this the diffusive and convective transport properties can be adjusted by fine tuning the morphology, i.e. structure, of the inner layer. Due to this layer structure the mechanical properties can be further increased.

In a further embodiment the hollow fiber membrane has a hydraulic permeability within the range of $1 \times 10^{-4}$-$100 \times 10^{-4}$ [$cm^3/cm^2 \times bar \times s$], preferably within the range of $1 \times 10^{-4}$ to $70 \times 10^{-4}$ [$cm^3/cm^2 \times bar \times s$], and most preferably within the range of $1 \times 10^{-4}$ to $27 \times 10^{-4}$ [$cm^3/cm^2 \times bar \times s$]. With this hydraulic permeability the convective transport through the membrane wall is minimized at the same time having high diffusive transport in a broad range with respect to the molecular size (up to 100.000 Dalton depending on the fluid and measurement condition) or shape of the molecule.

In another embodiment the hollow fiber membrane comprises a polymer composition comprising polysulphone (PSU), polyethersulphone (PES) or polyarylethersulphone (PAES); and polyvinylpyrrolidone (PVP).

In even another embodiment the polyvinylpyrrolidone (PVP) in the membrane comprises a blend of at least two homo-polymers of polyvinylpyrrolidone (PVP), and wherein one of the homo-polymers has an average relative molecular weight within the range of 10.000 g/mole to 100.000 g/mole, preferably within the range of 30.000 g/mole to 60.000 g/mole (=low molecular weight PVP), and another one of the homo-polymers has an average relative molecular weight within the range of 500.000 g/mole to 2.000.000 g/mole, preferably within the range of 800.000 g/mole to 2.000.000 g/mole (=high molecular weight PVP).

In one embodiment the hollow fiber membrane has an inner diameter within the range of 50 to 2000 μm, preferably within the range of 104 to 1464 μm.

In one embodiment the hollow fiber membrane has a wall thickness within the range of 10 to 200 ∞m, preferably within the range of 22 to 155 μm.

In another embodiment the hollow fiber membrane has an effective diffusion coefficient through the membrane for urea (60 g/mole) of $4 \times 10^{-6}$ to $15 \times 10^{-6}$ $cm^2/s$.

Further, the present invention concerns a process for manufacturing a semipermeable hollow fiber membrane, comprising the steps of extruding a polymer solution through an outer ring slit of a hollow fiber spinning nozzle, simultaneously extruding a bore liquid through the inner bore of the hollow fiber spinning nozzle, into a precipitation bath. According to the invention the polymer solution contains 10-20 wt.-% of polysulphone (PSU), polyethersulphone (PES) or polyarylethersulphone (PAES), 2-15 wt.-% polyvinylpyrrolidone (PVP) and a solvent, the bore liquid contains 50-75 wt.-% of a solvent and 25-50 wt.-% of water, the precipitation bath contains 50-70 wt.-% of a solvent and 30-50 wt.-% of water and has a temperature within the range of 22-31° C., and the distance between the discharge outlet of the hollow fiber spinning nozzle and the surface of the precipitation bath is within the range of 0-10 cm.

In one embodiment of the process according to the invention, the precipitation bath contains 52-69 wt.-% of a solvent and 31-48 wt.-% of water.

In another embodiment of the process according to the invention, the solvent in the polymer solution, the bore liquid and the precipitation bath is chosen from N-methylpyrrolidone, N-ethylpyrrolidone, N-octylpyrrolidone, dimethylacetamide, dimethylformamide, dimethyl sulphoxide, gamma-butyrolactone or mixtures thereof.

In even another embodiment of the process according to the invention, the solvent in the polymer solution, the bore liquid and the precipitation bath is chosen from is N-methylpyrrolidone, N-ethylpyrrolidone, N-octylpyrrolidone or mixtures thereof, preferably N-methylpyrrolidone.

In a further embodiment of the process according to the invention, the polymer solution contains 17-18 wt.-% of polysulphone (PSU), polyethersulphone (PES) or polyarylethersulphone (PAES), 8-11.25 wt.-% of polyvinylpyrrolidone (PVP) and 70-75 wt.-% of a solvent.

In another embodiment of the process according to the invention, the polyvinylpyrrolidone (PVP) in the polymer solution comprises a blend of at least two homo-polymers of polyvinylpyrrolidone (PVP), and wherein one of the homo-polymers has an average relative molecular weight within the range of 10.000 g/mole to 100.000 g/mole, preferably within the range of 30.000 g/mole to 60.000 g/mole (=low molecular weight PVP), and another one of the homo-polymers has an average relative molecular weight within the range of 500.000 g/mole to 2.000.000 g/mole, preferably within the range of 800,000 g/mole to 2.000.000 g/mole (=high molecular weight PVP).

In another embodiment of the process according to the invention, the polymer solution, based on the total weight of the polymer solution, contains the low molecular weight PVP in an amount of 1-10 wt.-%, preferably in an amount of 5-8 wt.-%, and the high molecular weight PVP in an amount of 1-5 wt.-%, preferably in an amount of 3-3.25 wt.-%. In even another embodiment of the process according to the invention, the precipitation bath has a temperature within the range of 22-27° C.

In a further embodiment of the process according to the invention, the hollow fiber spinning nozzle is held at a temperature within the range of 40-70° C., preferably within the range of 54-60° C.

In one embodiment of the process according to the invention, the distance between the discharge outlet of the hollow fiber spinning nozzle and the surface of the precipitation bath is within the range of 0-4 cm. The discharge outlet is the outlet where the polymer solution enters out of the spinning nozzle.

In another embodiment of the process according to the invention, the spinning speed of the hollow fiber membrane is 5-70 m/min, preferably 7.5-45 m/min.

In another embodiment of the process according to the invention the polymer solution has a viscosity, measured at room temperature, within a range of 10 000 to 100 000 mPa×s, preferably within the range of 21 500 to 77 000 mPa×s.

The present invention further concerns the use of the hollow fiber membrane according to above, or prepared by the process according to above in hemodialysis, as a sensor membrane for direct blood contact, as a sensor membrane in water applications, such as waste water applications, and delivery membrane in biological processes.

There are at least three potential applications for this type of membrane. In all potential applications the outside of the membrane is in contact with a fluid that has the potential to foul the membrane. However, there might be additional applications were this is not the case.

Commercial membranes, e.g. having the selective layer on the inside and pores in the μm range on the outside, will either block or lead to haemolysis in blood based applications if blood where brought in contact with the outer wall surface. In the following applications the membrane described in this patent application shows clear advantages.

The membrane according to the present invention could be used as hemodialysis membrane where the blood is in contact with the outside of the membrane. For this application, the outside of the membrane should have an equal pore size, diffusion coefficient, and material composition and roughness as the inside of commercial dialysis membranes, which have the blood contacting surface on the inside of the dialysis membrane. Depending on the pore size, the transport kinetics through the membrane might be dominated by diffusion. If the pore sizes were increased and the low roughness were kept, the transport kinetics could be based on a combination of diffusion and convection. The smooth outer surface of the membrane is required to not allow blood cells and high molecular weight proteins to enter the porous membrane structure. If blood cells and high molecular weight proteins where to enter the porous membrane structure, this could lead to rupture of the blood cells and formation of protein layers in the structure. Both effects are not acceptable in this application.

The membrane according to the present invention could also be used as a sensor membrane (micro-dialysis) for direct blood applications. If micro-dialysis in direct blood applications is performed, fouling of the membrane is a severe problem. Cells can enter the outside of the membrane if pores exceed a few μm in diameter. At the same time high molecular weight proteins can enter the porous structure of the membrane. This leads to pore blocking and the generation of a protein layer inside the porous membrane structure of the wall. In an extreme case, the outer surface of the membrane could lead to clot formation. Therefore a highly biocompatible surface is required for this type of application. The same counts for the application as dialysis membrane.

The membrane according to the present invention could further be used as a sensor membrane in (waste) water applications. In these applications it is important to analyze the ion concentration to control the composition of waste water or analyze the content of ions in water samples. To simplify the analysis, only the ions should pass through the membrane and not high molecular weight substances. For this application the transport should be based mainly on diffusion. A high amount of convective transport would dilute the analysis system. At the same time the transport of the ions should be stable over days, weeks or month. Therefore the outside of the membrane should have low fouling properties. This again is achieved by a combination of material properties, pore size and surface roughness.

The membrane according to the present invention could further be used as a delivery membrane in biological processes. In fermenter systems it might be necessary to control the amount of a fluid or substance that is added to the process over time. To allow an extremely homogeneous dilution of such substances a hollow fiber membrane hanging in a stirred tank reactor having a smooth outer surface and tailor made diffusion characteristics is of use.

This is of course only some possible applications of the membrane according to the present invention. There might be a vast number of other applications out there, which would benefit from this type of tailor made membrane. In general, the advantages and properties of the membrane according to the invention can be summarized as follows:

Most narrow pore size on the outside of the membrane
Smooth surface on the outside
Low protein adsorption properties of the outside structure
Highly biocompatible surface of the outside structure (i.e. low thrombogenicity)
Hydraulic permeability between $1 \times 10^{-4}$ and $100 \times 10^{-4}$ $cm^3/(cm^2\ bar\ sec)$
Hydrophilic—spontaneous wetting membrane
Sponge-like structure
Inner diameter between 50 and 2000 μm
Wall thickness between 10 and 200 μm
Transport based on diffusion or on diffusion and convection
Mechanical stability
Thin selective layer allowing high mass transfer rates To allow manufacturing of skin outside membranes by a diffusion induced phase separation (DIPS) procedure a number of criteria have to be fulfilled.

The porous structure behind the "selective" outer surface in direction to the lumen side has larger pores up to several μm. The porous structure is gained by a slow phase separation process. To allow a slow phase separation process the amount of a solvent (solvent for the polymer) has to be sufficient high. However, high concentration of a solvent in the bore liquid (could also be called the center fluid, which is introduced in the bore or center of the hollow fiber during the precipitation procedure) and the precipitation bath creates instability of the fiber. This makes it difficult to get stable fibers into the precipitation bath and out of this bath. The challenge is to adjust the solvent concentration during the precipitation procedure (in the center and the precipitation bath) and the precipitation bath temperature in such a way that it allows the creation of a membrane that has smaller pores on the outer surface than on the inner surface in addition with a very smooth outer surface for good biocompatibility.

The challenge is to find a production window that allows to adjust (i) sufficiently high concentration of solvent in the center to generate a very open structure that allows a small mass transfer resistance over the membrane, (ii) a solvent concentration in the precipitation bath to get a smooth surface structure on the outside of the membrane with pores in the selective layer within the range of 1 to 10 nm in combination with a highly biocompatible surface (material composition, roughness and so on), and (iii) stable spinning conditions. The major process parameters on the spinning machine are:

polymer composition in the polymer solution
temperature of the spinning nozzle
design of the spinning nozzle
distance between spinning nozzle and precipitation bath
conditions in the atmosphere between spinning nozzle and precipitation bath
dimensions of the hollow fiber
composition of the bore liquid
composition of the precipitation bath
temperature of the precipitation bath spinning speed time/distance the fiber is moving through the precipitation bath The mentioned parameters are not complete. This is just to give an indication about the process parameters and the complexity.

When the polymer solution has been prepared, see e.g. Example 1 for this information, the polymer solution is pumped through a spinning nozzle and the liquid hollow fiber is formed. The solvent concentration in the bore liquid leads to an open structure at the inner side of the membrane. The distance between the spinning nozzle and the precipitation bath, the concentration range of solvent in the precipitation bath and the time and the distance the fiber is moving through the precipitation bath, leads to a very smooth surface structure on the outer surface. In one embodiment of the process according to the invention, the time in the precipitation bath is between 2 and 60 seconds.

The smallest pores are at the outer side of the membrane. The overall structure and the pores at the inside of the membrane are much larger. The selective layer at the outside is intended for direct blood contact. The challenge is to adjust the spinning conditions to fulfill the profile of the membrane, i.e. biocompatibility, a small mass transfer resistance and so forth.

The temperature and the solvent concentration in the precipitation bath interact strongly with each other. Increasing the temperature would allow to decrease the solvent concentration, resulting in the same structure of morphology, pore size and hydraulic permeability. However, there are technical limits when increasing the temperature of the precipitation bath.

The biocompatibility of the membrane is proven to be very good based on the comparable characteristics of the selective layer of a regular dialysis membrane (inside) and the morphology and characteristics of the outside layer of this special membrane. However, to even increase this further it might be of value to functionalize the outer surface of the membrane. One option could be to covalently bind heparin to the surface. To allow covalent binding of heparin, the membrane could be treated with plasma ignition together with a precursor gas containing functional groups as disclosed in WO2006/006918 or in WO03/090910.

BRIEF DESCRIPTION OF THE DRAWING(S)

FIG. 2a to 2d show a hollow fiber membrane according to another embodiment of the present invention, produced according to example 2 below.

FIG. 3a to 3d show a hollow fiber membrane according to another embodiment of the present invention, produced according to example 3 below.

MATERIAL AND METHODS

Figure 1A:
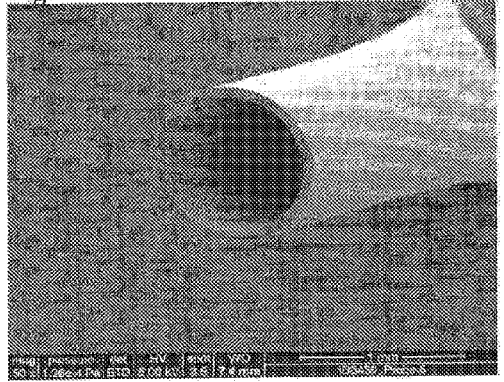
FIG. 1a to 1d show a hollow fiber membrane according to one embodiment of the present invention, produced according to example 1 below.
Figure 1B:
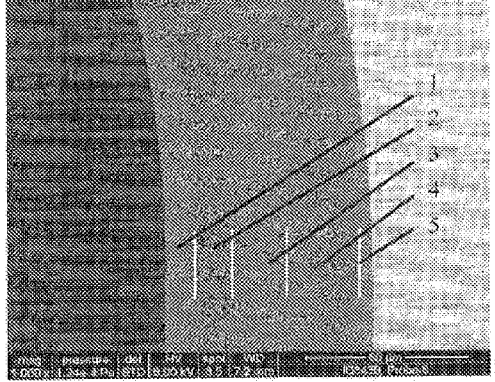
Figure 1C:
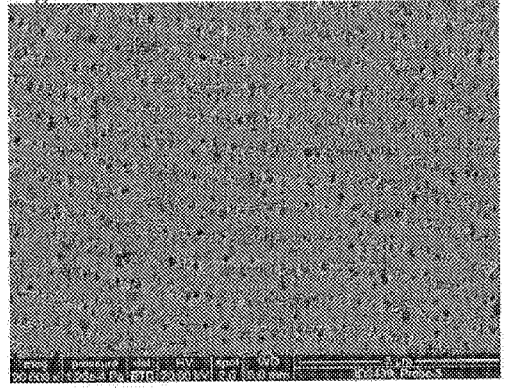
Figure 1D:
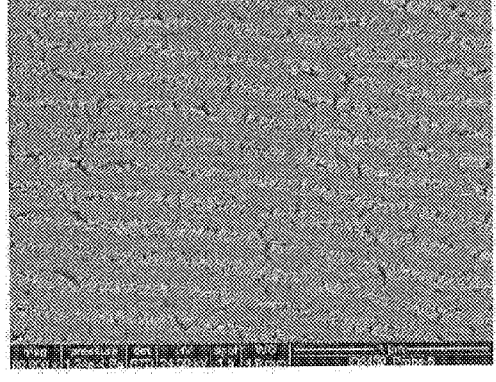

AFM Analysis:

The AFM studies have been preformed using an Atomic Force Microscope from Digital Instruments/Veeco, Type: NanoScope IIIa Multi Mode. To minimize the interaction between the measurement probe and the membrane material/membrane surface, the data is obtained using the Tapping Mode. This allows to the generation of stable pictures/data from the surface topography of the outer membrane surface. Due to the extremely smooth surface and the small pores of the outer surface of the hollow fiber membranes special probes having a small radius at the tip of the probe, are used. The tips used for the measurement in this application (from Nanosensors, Type SSS-NCH (Super Sharp Silicon)) had a typical tip angle of $R\approx 2$ nm. Some samples, having a slightly higher surface roughness, have been measured using a NCH (Nanosensors) tip with a typical tip angle of $R\approx 10$ nm. The samples measured have a size of 2×2 μm or a size of 5×5 μm.

To perform the measurement the membrane samples have been placed on a flat substrate using double-sided adhesive tape. Surface areas of 5 μm×5 μm, 2 μm×2 μm, and 1 μm×1 μm have been characterised using the atomic force microscope (AFM). Every single data set of the different pictures shown are analysed, calculating different roughness parameter ($R_a$, $R_q$) using the following equations:

$$R_q = \sqrt{\frac{1}{N}\sum_{i=1}^{N} Z_i^2}$$

$$R_a = \frac{1}{N}\sum_{i=1}^{N} |Z_i|$$

with N=Total number of data points and $Z_i$=Height of a data point above the average picture level Membrane Bundle Preparation:

Preparation of Hand Bundles:

The preparation of the membrane bundle after the spinning process is necessary in order to prepare the fiber bundle in an adequate way for succeeding performance tests. The first process step is to cut the fiber bundles to a defined length of 23 cm. The next process step consists of closing the ends of the fibers. An optical control ensures that all fiber ends are closed. Then, the ends of the fiber bundle are transferred into a potting cap. The potting cap is fixed mechanically and a potting tube is put over the potting caps. Afterwards, the potting is done with polyurethane. After the potting it has to be ensured that the polyurethane can harden for at least one day. In the next process step, the potted membrane bundle is cut to a defined length. The last process step consists of an optic control of the fiber bundle. During this process step, the following points are controlled:

⇒ Quality of the cut (is the cut smooth or are there any damages created by the knife);

⇒ Quality of the potting (is the number of open fibers of the spinning process reduced by fibers that are potted, or are there any visible voids where there is no polyurethane).

After the optical control, the membrane bundles are stored dry before they are used for the different performance tests.

Preparation of Mini-Modules:

Mini-modules [=fiber bundles in a housing] are prepared with related process steps. The mini-modules are needed to ensure a protection of the fibers and a very clean manufacturing method as the biocompatibility tests are carried out with human plasma. The manufacturing of the mini-modules differs in the following points:
- The fiber bundle is cut to a defined length of 20 cm;
- the fiber bundle is transferred into the housing before closing the fiber ends; and
- the mini-module is put into a vacuum drying oven over night before the potting process.

Figure 7:
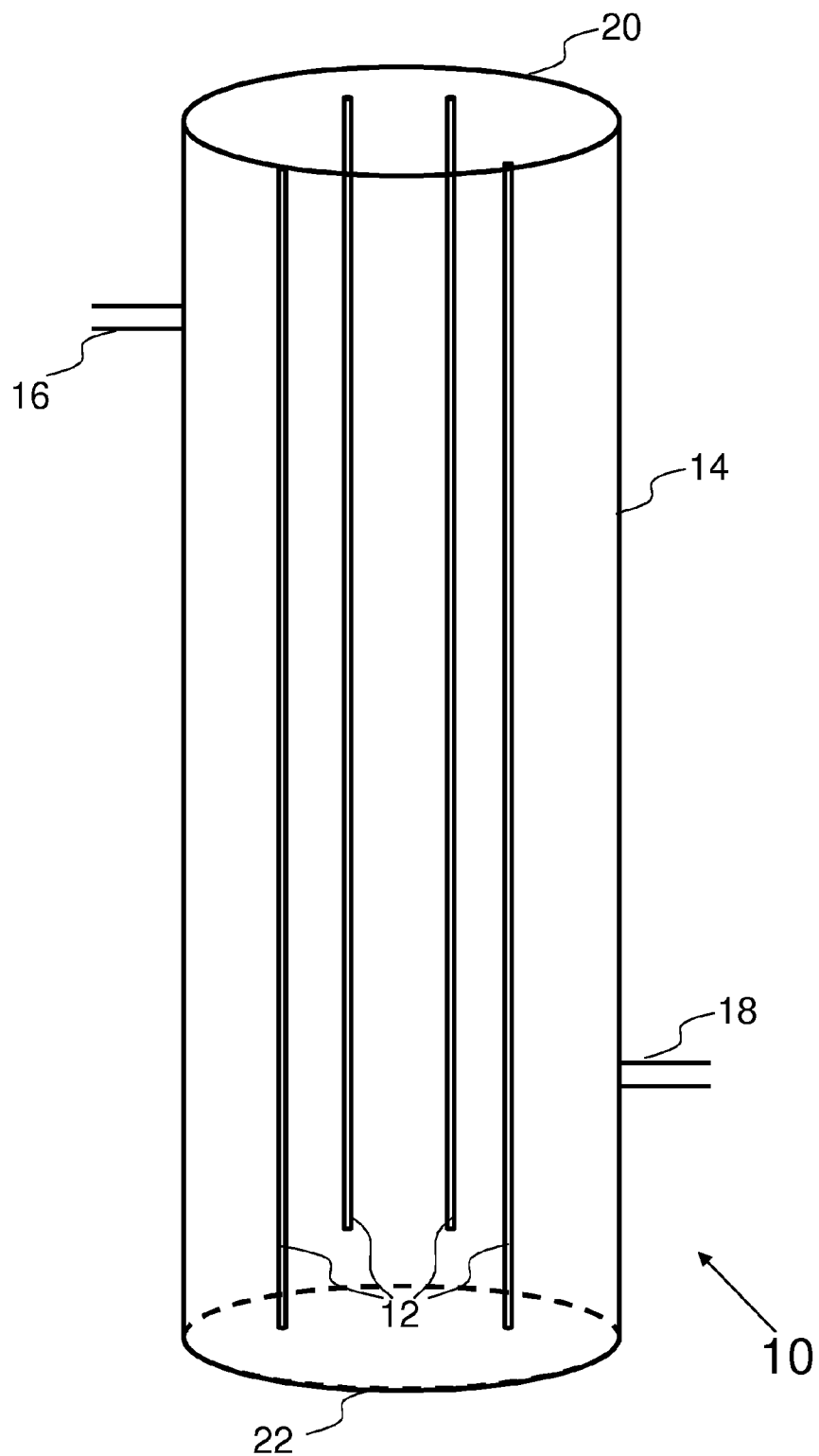
FIG. 7 is a perspective view of the device according to one embodiment.

Preparation of Filters:

According to the embodiment illustrated in FIG. 7, the filter (=dialyzer) 10 has around 8,000-10,000 fibers 12 with an effective surface area of 0.5 to 0.6 m². A filter 10 is characterized by a cylindrical housing 14 with two connectors 16, 18 for the dialyzing fluid and applied caps 20, 22 on both sides, each with one centred blood connector. The manufacturing process (after winding) can be split up into the following main steps:
- The cut (length of 20 cm) bundles are transferred into the housing with a special bundle claw;
- both ends of the bundles are closed;
- potting the fibers into the housing with Polyurethane (PUR);
- cutting of the ends to open the fibers, wherein a smooth surface is required;
- visual control of the ends for closed fibers or imperfections in the PUR block; and
- gluing of the caps with the blood connectors.

Hydraulic Permeability (Lp) of Hand Bundles and Mini-Modules:

From Inside to Outside (Hand Bundles):

The hydraulic permeability of a membrane bundle is determined by pressing an exact defined volume of water under pressure through the membrane bundle, which is closed on one side of the bundle and measuring the required time. The hydraulic permeability can be calculated with the determined time, the effective membrane surface area, the applied pressure and the volume of water, which is pressed through the membrane. The effective membrane surface area can be calculated by the number of fibers, the fiber length and the inner diameter of the fiber. The membrane bundle has to be wetted thirty minutes before the test is performed. Therefore, the membrane bundle is put in a box containing 500 ml of ultrapure water. After 30 minutes, the membrane bundle is transferred into the testing system. The testing system consists of a water bath that has a temperature of 37° C. and a device where the membrane bundle can be implemented mechanically. The filling height of the water bath has to ensure that the membrane bundle is located underneath the water surface in the designated device. To avoid that a leakage of the membrane leads to a wrong test result, an integrity test of the membrane bundle and the test system has to be carried out in advance. The integrity test is performed by pressing air through the membrane bundle which is dosed on one side of the bundle. Air bubbles indicate a leakage of the membrane bundle or the test device. It has to be checked if the leakage can be associated with the wrong implementation of the membrane bundle in the test device, or if a real membrane leakage is present. The membrane bundle has to be discarded, if a leakage of the membrane is detected. The applied pressure of the integrity test has to be at least the same value as the applied pressure during the determination of the hydraulic permeability, in order to ensure that no leakage can occur during the measurement of the hydraulic permeability, because of a too high applied pressure.

From Outside to Inside (Minimodules):

The measurements were carried out following the same measuring principle as mentioned in the measurement from inside to outside.

Hydraulic Permeability (Lp) of Filters:

From Inside to Outside:

In difference to testing procedure at hand bundles, the hydraulic permeability of a filter is determined by flowing an exactly defined volume of water through the membrane, and the trans membrane pressure is measured. Before starting the measurement, the filter has to be totally filled (inside the membrane and the compartment between the housing and the membranes) with the testing fluid. Air is thereby removed by easy knocking. The testing fluid, pure water with a sodium chloride concentration of 0.9%, is set to a temperature of 38° C. and is thereby pumped to the blood inlet of the filter, whereby the exit blood connector and the entrance of the dialyzed connection are closed. The measurement takes 5 minutes and average values for the pressures are calculated. The calculation of the hydraulic permeability is equal to the description for the hand bundles/mini modules.

From Outside to Inside:

The principle of the measurement is the same as for measuring from inside to outside, except of filtration of the pure water in backward direction. In this, the fluid is pumped to the dialysate inlet and the blood inlet as well as the dialysate exit is closed.

Permeability Tests/Diffusion Experiment of Hand Bundles:

Diffusion experiments with isotonic chloride solution are carried out to determine the diffusion properties of a membrane. A hand bundle is put in a measuring cell. The measuring cell allows to pass the chloride solution at the inside of the hollow fiber. Additionally, the measuring cell is filled completely with water, and a high cross flow of distilled water is set to carry away the chloride ions that pass the membrane cross section from the inside of the hollow fiber to the outside. By adjusting the pressure ratios correctly, a zero filtration is aimed for so that only the diffusion properties of the membrane are determined (by achieving the maximum concentration gradient of chloride between the inside of the hollow fiber and the surrounding of the hollow fiber) and not a combination of diffusive and convective properties. A sample from the pool is taken at the beginning of the measurement and a sample of the retentate is taken after 10 and 20 minutes. The samples are then titrated with a silver nitrate solution to determine the chloride concentration. With the obtained chloride concentrations, the effective membrane surface area and the flow conditions, the chloride permeability can be calculated. The same set-up can be used to analyse the permeability of other substances/proteins. Tests have been performed using urea as test substance. The concentration of urea in the different solutions is quantified using standard methods. The method used to determine the permeability ($P_m$) is described by Elias Klein et. al.

E. Klein, F. F. Holland, A. Donnaud, A. Lebeouf, K. Eberle, "Diffusive and hydraulic permeabilities of commercially available hemodialysis films and hollow fibers", Journal of Membrane Science, 2 (1977) 349-364.

E. Klein, F. F. Holland, A. Lebeouf, A. Donnaud J. K. Smith, "Transport and mechanical properties of hemodialysis hollow fibers", Journal of Membrane Science, 1 (1976) 371-396.

Further Literature: References in the articles of E. Klein mentioned.

The effective diffusion coefficient ($D_{Meff}$) of a certain substance (substance, ion, or protein) is related to the membrane diffusive permeability ($P_m$) of this substance by $D_{Meff} = P_m \times \Delta z$, where $\Delta z$ is the diffusive distance (wall thickness of the membrane).

Viscosity Measurements:

The term "viscosity" in respect of the polymer solution of the present invention means the dynamic viscosity, if not otherwise indicated. The unit of the dynamic viscosity of the polymer solution is given in Centipoise (cp) or mPa×s. To measure the viscosity of the polymer solution, a commercial rheometer from Rhemoetic Scientific Ltd. (SR 2000) was used. The polymer solution is placed between two temperature-controlled plates. The measurement is performed at 22° C. All other measurement condition are according to the manufacturer's instructions.

EXAMPLES

Example 1

A polymer solution is prepared by dissolving polyethersulphone (BASF Ultrason 6020) and polyvinylpyrrolidone (PVP) (BASF K30 and K85) in N-methylpyrrolidone (NMP). The weight fraction of the different components in the polymer spinning solution was: PES-PVP K85-PVP K30-NMP: 18-3,25-8-70,75. The viscosity of the polymer solution was 53560 mPa×s.

To prepare the solution NMP is first filled into a three neck-flask with finger-paddle agitator in the center neck. The PVP is added to the NMP and is stirred at 50° C. until a homogeneous clear solution is prepared. Finally, the polyethersulphone (PES) is added. The mixture is stirred at 50° C. until a clear high viscous solution is obtained. The warm solution is cooled down to 20° C. and degassed. To fully degas the solution, the highly viscous polymer solution is transferred into a stable stainless steel container. Thereafter the container is closed tightly and vacuum is applied to the container. The solution is degassed at 50 mmHg for 6 hours. During this degassing procedure the container is rotated to create a larger surface and thinner film thickness of the polymer solution in the container, to improve the degassing procedure.

A membrane is formed by heating the polymer solution to 50° C. and passing the solution through a spinning nozzle (also called spinning die or spinneret). As bore liquid, a water and NMP mixture containing 42 wt.-% water and 58 wt.-% NMP is used. The temperature of the spinning nozzle is 55° C. The hollow fiber membrane is formed at a spinning speed of 10 m/min. The liquid capillary leaving the spinning nozzle is passed into a NMP/water bath (NMP concentration is 52%) having a temperature of 26° C. The length of the distance between the spinning nozzle and the precipitation bath is 4 cm. The formed hollow fiber membrane is guided through a water bath having a temperature of 65° C. The wet hollow fiber membrane has an inner diameter of 1012 µm, an outer diameter of 1152 µm and a fully asymmetric membrane structure. The active separation layer of the membrane is at the outer wall surface. The active separation layer is defined as the layer with the smallest pores. The hydraulic permeability (Lp value) of the membrane was measured from inside to outside in a hand bundle, using the methods described earlier. The membrane showed a hydraulic permeability of $3.5 \times 10^{-4}$ cm$^3$/(cm$^2$ bar sec).

In FIG. 1$a$, a scanning electron micrograph of the cross-section of the hollow fiber membrane is shown. In FIG. 1$b$ a close up of the cross-section of the hollow fiber wall is shown and, as is evident from the picture, the wall has an asymmetric structure and the overall structure is a sponge-like structure. There are five different layers within the hollow fiber wall, and these different layers have been marked up, and as could be seen from the picture, the different layers have different pore sizes and different mass densities. The first layer is the outer selective layer and this layer has the smallest pores and the highest mass density. The second layer has larger pores and lower mass density than the first layer. The third layer has smaller pores and higher mass density than the second layer, but larger pores and lower mass density than the first layer. The fourth layer has larger pores and lower mass density than all of first, second and third layer. The fifth layer has smaller pores and higher mass density than the fourth layer. In FIG. 1$c$ the inner wall surface is shown, and in FIG. 1$d$ the outer wall surface is shown and the outer wall surface is very smooth and have smooth pores.

The roughness of the outer wall surface was measured and calculated as disclosed above with a probe having a tip angle of R≈2 nm. For a sample of the size 2×2 µm, the roughness parameters were $R_a$ 4.9 nm and $R_q$ 6.3 nm, and for a sample of the size 5×5 µm, the roughness parameters were $R_a$ 7.9 nm and $R_q$ 10.0 nm.

Example 2

The second example has been carried out with the identical composition of the polymer solution as in Example 1. The viscosity of the polymer solution was 60200 mPa×s.

The polymer preparation procedure was kept as described in Example 1. The membrane formation procedure was changed for the following points:

⇨ Temperature of the spinning nozzle: 54° C.
⇨ Spinning velocity: 7.5 m/min
⇨ Distance between the spinning nozzle and the precipitation bath: 2.5 cm
⇨ Temperature of the precipitation bath: 27° C.

The remaining process steps are kept as in example 1. The wet hollow fiber membrane has an inner diameter of 1464 µm, an outer diameter of 1592 µm and a fully asymmetric membrane structure. The active separation layer of the membrane is at the outer wall surface. The active separation layer is defined as the layer with the smallest pores. The hydraulic permeability (Lp value) of the membrane is measured from inside to outside in a hand bundle, using the methods described earlier. The membrane showed a hydraulic permeability of $3.4 \times 10^{-4}$ cm$^3$/(cm$^2$ bar sec).

In FIG. 2$a$, a scanning electron micrograph of the cross-section of the hollow fiber membrane is shown. In FIG. 2$b$ a close up of the cross-section of the hollow fiber wall is shown and, as is evident from the picture, the wall has an asymmetric structure and the overall structure is a sponge like structure. There are five different layers within the hollow fiber wall, and these different layers have been marked up, and as could be seen from the picture the different layers have different pore sizes and different mass densities. The first layer is the outer selective layer and this layer has the smallest pores and the highest mass density. The second layer has larger pores and lower mass density than the first layer. The third layer has smaller pores and higher mass density than the second layer, but has larger pores and lower mass density than the first layer. The fourth layer has larger pores and lower mass density than all of the first, second and third layers. The fifth layer has smaller pores and higher mass density than the fourth layer. In FIG. 2$c$ the inner wall surface is shown, and in FIG. 2$d$ the outer wall surface is shown and the outer wall surface is very smooth and have smooth pores.

The roughness of the outer wall surface was measured and calculated as disclosed above with a probe having a tip angle of R≈2 nm. For a sample of the size 2×2 μm, the roughness parameters were $R_a$ 1.9 nm and $R_q$ 2.4 nm, and for a sample of the size 5×5 μm, the roughness parameters were $R_a$ 2.8 nm and $R_q$ 3.6 nm.

Example 3

The third example has been carried out with the identical composition of the polymer solution as in Example 1. The viscosity of the polymer solution was 59300 mPa×s.

The polymer preparation procedure was kept as described in Example 1. The membrane formation procedure was changed for the following points:
- Bore liquid ($H_2O$: NMP) 38 wt.-%:62 wt.-%
- Concentration of NMP in the precipitation bath: 64 wt.-%
- Distance between the spinning nozzle and the precipitation bath: 3 cm
- Temperature of the precipitation bath: 22° C.

The remaining process steps are kept as in Example 1. The only difference is that the fiber had different dimensions. The hollow fiber membrane has an inner diameter of 203 μm, an outer diameter of 281 μm and a fully asymmetric membrane structure. The active separation layer of the membrane is at the outer wall surface. The active separation layer is defined as the layer with the smallest pores. The hydraulic permeability (Lp value) of the membrane is measured from inside to outside in a hand bundle and from outside to inside in a mini-module using the methods described earlier. The membrane showed a hydraulic permeability of $6.7 \times 10^{-4}$ cm$^3$/(cm$^2$ bar sec) when measured from inside to outside and $6.7 \times 10^{-4}$ cm$^3$/(cm$^2$ bar sec) when measured from outside to inside.

In FIG. 3a, a scanning electron micrograph of the cross-section of the hollow fiber membrane is shown. In FIG. 3b a close-up of the cross-section of the hollow fiber wall is shown and, as is evident from the picture, the wall has an asymmetric structure and the overall structure is a sponge like structure. There are four different layers within the hollow fiber wall, and these different layers have been marked up, and as could be seen from the picture, the different layers have different pore sizes and different mass densities. The first layer is the outer selective layer and this layer has the smallest pores and the highest mass density. The second layer has larger pores and lower mass density than the first layer. The third layer has smaller pores and higher mass density than the second layer, but has larger pores and lower mass density than the first layer. The fourth layer has larger pores and lower mass density than all of the first, second and third layers. In FIG. 3c the inner wall surface is shown, and in FIG. 3d the outer wall surface is shown, the outer wall surface being very smooth and with smooth pores.

The roughness of the outer wall surface was measured and calculated as disclosed above with a probe having a tip angle of R≈2 nm. For a sample of the size 2×2 μm, the roughness parameters were $R_a$ 3.3 nm and $R_q$ 4.2 nm, and for a sample of the size 5×5 μm, the roughness parameters were $R_a$ 4.6 nm and $R_q$ 5.7 nm.

Example 4

The fourth example has been carried out with the identical composition of the polymer solution as in Example 1. The viscosity of the polymer solution was 62100 mPa×s.

The polymer preparation procedure was kept as described in Example 1. The membrane formation procedure was changed for the following points:
- Bore liquid ($H_2O$:NMP) 38 wt.-%:62 wt.-%
- Concentration of NMP in the precipitation bath: 69 wt.-%

The remaining process steps are kept as in Example 1. The only difference is that the fiber had different dimensions. The hollow fiber membrane has an inner diameter of 311 μm, an outer diameter of 395 μm and a fully asymmetric membrane structure. The active separation layer of the membrane is at the outer wall surface. The active separation layer is defined as the layer with the smallest pores. The hydraulic permeability (Lp value) of the membrane is measured from inside to outside in a hand bundle using the methods described earlier. The membrane showed a hydraulic permeability of $27.0 \times 10^{-4}$ cm$^3$/(cm$^2$ bar sec).

Figure 4A:
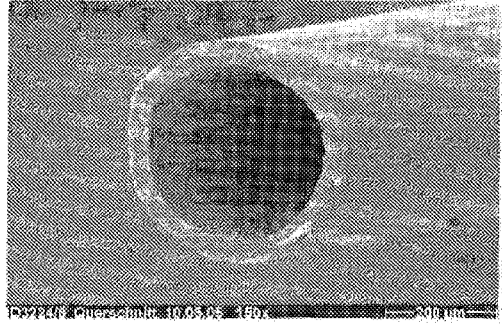
FIG. 4a to 4d show a hollow fiber membrane according to another embodiment of the present invention, produced according to example 4 below.
Figure 4B:
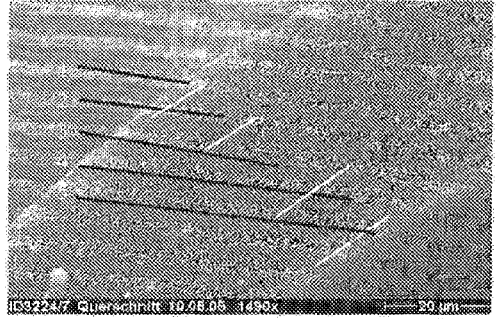
Figure 4C:
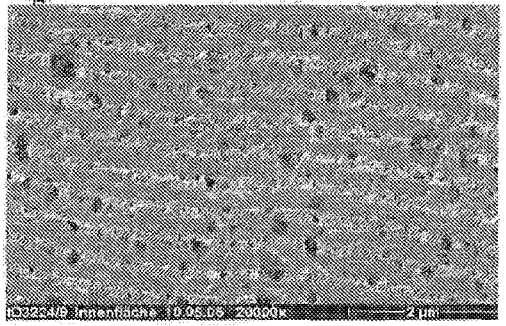
Figure 4D:
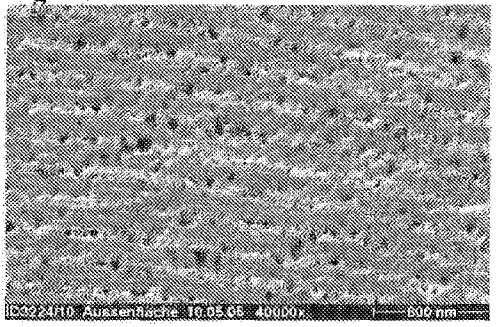

In FIG. 4a, a scanning electron micrograph of the cross-section of the hollow fiber membrane is shown. In FIG. 4b a close-up of the cross-section of the hollow fiber wall is shown and, as is evident from the picture, the wall has an asymmetric structure and the overall structure is a sponge-like structure. There are five different layers within the hollow fiber wall, and these different layers have been marked up, and as could be seen from the picture, the different layers have different pore sizes and different mass densities. The first layer is the outer selective layer and this layer has the smallest pores and the highest mass density. The second layer has larger pores and lower mass density than the first layer. The third layer has smaller pores and higher mass density than the second layer, but has larger pores and lower mass density than the first layer. The fourth layer has larger pores and lower mass density than all of the first, second and third layers. The fifth layer has smaller pores and higher mass density than the fourth layer. In FIG. 4c the inner wall surface is shown, and in FIG. 4d the outer wall surface is shown, the outer wall surface being very smooth and with smooth pores.

The roughness of the outer wall surface was measured and calculated as disclosed above with a probe having a tip angle of R≈2 nm. For a sample of the size 2×2 μm, the roughness parameters were $R_a$ 4.6 nm and $R_q$ 5.9 nm, and for a sample of the size 5×5 mm, the roughness parameters were $R_a$ 7.2 nm and $R_q$ 9.1 nm.

Example 5

The polymer preparation procedure was kept as described in Example 1. The viscosity of the polymer solution was 53560 mPa×s. The membrane formation procedure was changed for the following points:
- Bore liquid ($H_2O$:NMP) 34 wt. %:wt.-66%
- Temperature of the spinning nozzle: 60° C.
- Spinning velocity: 45 m/min
- Distance between the spinning nozzle and the precipitation bath: 0 cm
- NMP concentration in the precipitation bath: 62 wt.-%
- Temperature of the precipitation bath: 25° C.

The remaining process steps are kept as in Example 1. The hollow fiber membrane has an inner diameter of 117 μm, an outer diameter of 163 μm and a fully asymmetric membrane structure. The active separation layer of the membrane is at the outer side. The active separation layer is defined as the layer with the smallest pores. The hydraulic permeability (Lp value) of the membrane is measured from inside to outside in a filter using the methods described earlier. The membrane showed a hydraulic permeability of $13.6 \times 10^{-4}$ cm$^3$/(cm$^2$ bar sec).

Figure 5A:
FIG. 5a to 5d show a hollow fiber membrane according to another embodiment of the present invention, produced according to example 5 below.
Figure 5B:
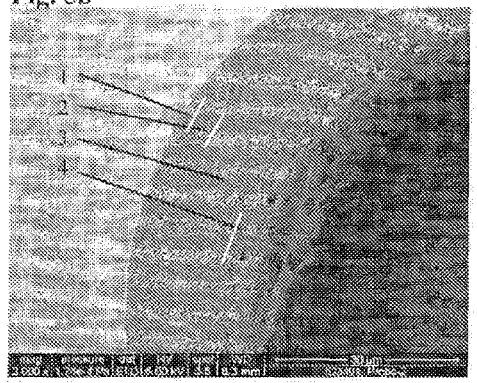
Figure 5C:
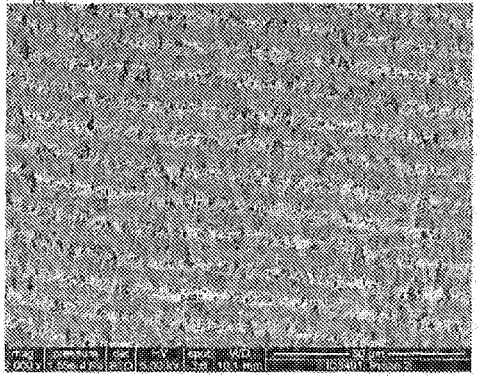
Figure 5D:
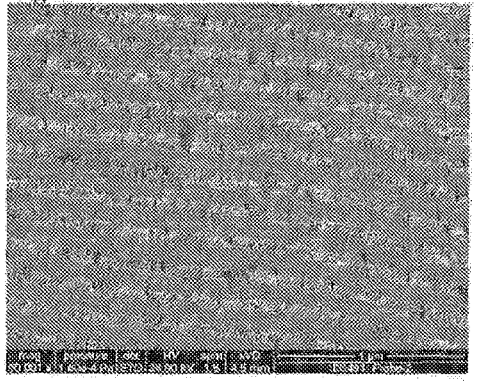

In FIG. 5a, a scanning electron micrograph of the cross-section of the hollow fiber membrane is shown. In FIG. 5b a close up of the cross-section of the hollow fiber wall is shown and, as is evident from the picture, the wall has an asymmetric structure and the overall structure is a sponge-like structure. There are four different layers within the hollow fiber wall, and these different layers have been marked up, and as could be seen from the picture, the different layers have different pore sizes and different mass densities. The first layer is the outer selective layer and this layer has the smallest pores and the highest mass density. The second layer has larger pores and lower mass density than the first layer. The third layer has smaller pores and higher mass density than the second layer, but has larger pores and lower mass density than the first layer. The fourth layer has larger pores and lower mass density than all of the first, second and third layers. In FIG. 5c the inner wall surface is shown, and in FIG. 5d the outer wall surface is shown, the outer wall surface being very smooth and with smooth pores.

The roughness of the outer wall surface was measured and calculated as disclosed above, with a probe having a tip angle of R≈10 nm. For a sample of the size 2×2 µm, the roughness parameters were $R_a$ 6.8 nm and $R_q$ 8.4 nm, and for a sample of the size 5×5 µm, the roughness parameters were $R_a$ 7.3 nm and $R_q$ 9.4 nm.

Comparative Example

The first experiment has been carried out with the identical composition of the polymer solution as in Example 1. The viscosity of the polymer solution was 62100 mPa×s.

The polymer preparation procedure was kept as described in example 1. The membrane formation procedure was changed for the following points:
⇒ Bore liquid ($H_2O$:NMP) 38 wt.-%:62 wt.-%
⇒ Concentration of NMP in the precipitation bath: 72 wt.-%

The remaining process steps are kept as in Example 1. The only difference is the point that the fiber had different dimensions. The hollow fiber membrane has an inner diameter of 312 µm, an outer diameter of 396 µm and a fully asymmetric membrane structure. The hydraulic permeability (Lp value) of the membrane is measured from inside to outside in a hand bundle using the methods described earlier. The membrane showed a hydraulic permeability of $120\times10^{-4}$ cm³/(cm² bar sec).

Figure 6A:
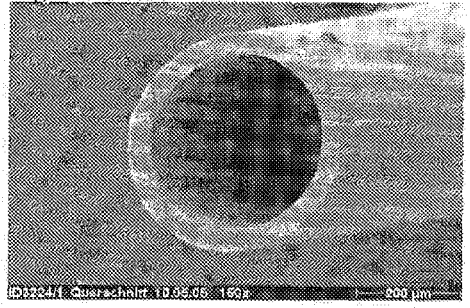
FIG. 6a to 6d show a comparative example of a hollow fiber membrane, produced according to the comparative example below.
Figure 6B:
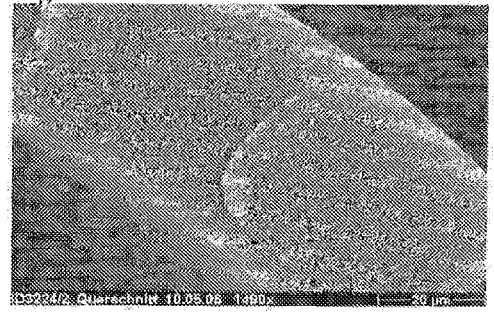
Figure 6C:
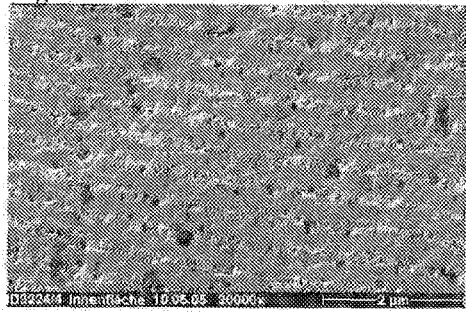
Figure 6D:
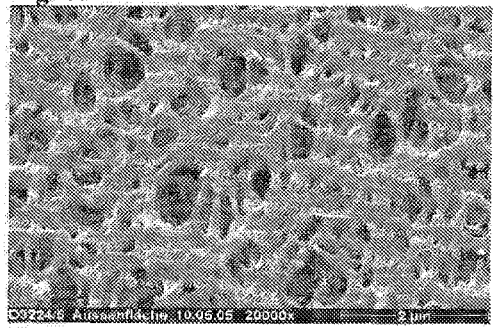

In FIG. 6a, a scanning electron micrograph of the cross-section of the hollow fiber membrane is shown. In FIG. 6b a close up of the cross-section of the hollow fiber wall is shown. In FIG. 6c the inner wall surface is shown, and in FIG. 6d the outer wall surface is shown. As is evident from FIG. 6c and FIG. 6d, the outer wall surface shows larger pores than the inner wall surface. Additionally, the smoothness of the outer wall surface has decreased and it is rougher.

The roughness of the outer wall surface was measured and calculated as disclosed above with a probe having a tip angle of R≈10 nm. For a sample of the size 2×2 µm, the roughness parameters were $R_a$ 19.8 nm and $R_q$ 26.4 nm, and for a serve of the size 5×5 µm, the roughness parameters were $R_a$ 23.3 nm and $R_q$ 30.5 nm, which is clearly outside the scope of the present invention.

It should be understood that various changes and modifications to the embodiments described herein, will be apparent to those skilled in the art. Such changes and modifications can be made without departing from the spirit and scope of the present invention, and without diminishing its attendant advantages. It is therefore intended that such changes and modifications be covered by the appended claims.

The invention claimed is:

1. A microdialysis device comprising:
a sensor membrane for direct blood applications, the sensor membrane being a semipermeable hollow fiber membrane comprising an outer wall surface being smooth, continuous, and homogeneous in a nanoscopic scale, an inner wall surface, and an interior lumen extending along the length of the semipermeable hollow fiber membrane, the semipermeable hollow fiber membrane having a selective layer on the outer wall surface, the outer wall surface having a smallest pore size and being virtually devoid of roughness with roughness parameters $R_a$ and $R_q$ of not more than 10 nm, roughness being measured with an atomic force microscope (AFM), and the roughness parameters $R_a$ and $R_q$ being calculated using the following equations:

$$R_a = \frac{1}{N}\sum_{i=1}^{N}|Z_i|$$

$$R_q = \sqrt{\frac{1}{N}\sum_{i=1}^{N}Z_i^2}$$

with N being the total number of data points and $Z_i$ being the height of a data point above an average picture level, wherein the semipermeable hollow fiber membrane comprises a membrane wall having at least four layers with different pore sizes and mass densities, and wherein a layer positioned closest to a middle of the membrane wall has a smaller pore size and a higher mass density than the two layers directly adjacent on each side of the layer positioned closest to the middle of the membrane wall.

2. The device of claim 1, wherein the membrane wall comprises four layers with different pore sizes and mass densities, and wherein a first layer, at the outer wall surface, has the smallest pore size and the highest mass density, wherein a second layer, adjacent to the first layer, has a larger pore size and lower mass density than the first layer, wherein a third layer, adjacent to the second layer, has a smaller pore size and higher mass density than the second layer, but a larger pore size and a lower mass density than the first layer, and a fourth layer, at the inner wall surface and adjacent to the third layer, has a larger pore size and a lower mass density than the first, second, and third layers.

3. The device of claim 1, wherein the membrane wall comprises five layers with different pore sizes and mass densities, wherein a first layer, at the outer wall surface, has the smallest pore size and the highest mass density, wherein a second layer, adjacent to the first layer, has larger pore size and lower mass density than the first layer, wherein a third layer, adjacent to the second layer, has smaller pore size and higher mass density than the second layer, but larger pore size and lower mass density than the first layer, a fourth layer, adjacent to the third layer, has a larger pore size and a lower mass density than the first, second and third layers, and a fifth layer, at the inner wall surface and adjacent to the fourth layer, has a larger pore size and a lower mass density than the first, second, third, and fourth layers.

4. The device of claim 1, wherein the membrane wall comprises five layers with different pore sizes and mass densities, wherein a first layer, at the outer wall surface, has the smallest pore size and the highest mass density, wherein a second layer, adjacent to the first layer, has larger pore size and lower mass density than the first layer, wherein a third layer, adjacent to the second layer, has smaller pore size and higher mass density than the second layer, but larger pore size and lower mass density than the first layer, a fourth layer, adjacent to the third layer, has a larger pore size and a lower mass density than the first, second, and third layers, and a fifth layer, at the inner wall surface and adjacent to the fourth layer, has a smaller pore size and a higher mass density than the fourth layer.

5. The device of claim 1, wherein the semipermeable hollow fiber membrane has a hydraulic permeability within the range of $1\times10^4$ to $100\times10^4$ [$cm^3/cm^2 \times bar \times s$].

6. The device of claim 1, wherein the semipermeable hollow fiber membrane comprises a polymer composition comprising polysulfone (PSU), polyethersulfone (PES) or polyarylethersulfone (PAES); and polyvinylpyrrolidone (PVP).

7. The device of claim 6, wherein the polyvinylpyrrolidone (PVP) in the semipermeable hollow fiber membrane comprises a blend of at least two homo-polymers of polyvinylpyrrolidone (PVP), and wherein one of the homo-polymers has an average relative molecular weight within the range of 10,000 g/mol to 100,000 g/mol, and another one of the homo-polymers has an average relative molecular weight within the range of 500,000 g/mol to 2,000,000 g/mol.

8. The device of claim 1, wherein the semipermeable hollow fiber membrane has an inner diameter within the range of 50 to 2000 μm.

9. The device of claim 1, wherein the semipermeable hollow fiber membrane has a wall thickness within the range of 10 to 200 μm.

10. The device of claim 1, wherein the semipermeable hollow fiber membrane has an effective diffusion coefficient through the membrane for urea (60 g/mol) within the range of $4\times10^{-6}$ to $15\times10^6$ [$cm^2/s$].

* * * * *